(12) United States Patent
Victor (10) Patent No.: US 6,586,013 B2
(45) Date of Patent: *Jul. 1, 2003

(54) METHOD OF USING OPTICALLY-ACTIVATED PARTICLES IN COSMETIC PREPARATIONS

(75) Inventor: Bruce H. Victor, Paterson, NJ (US)

(73) Assignee: Lipo Chemicals, Inc., Paterson, NJ (US)

( * ) Notice: Subject to any disclaimer, the term of this patent is extended or adjusted under 35 U.S.C. 154(b) by 46 days.

This patent is subject to a terminal disclaimer.

(21) Appl. No.: 09/872,648

(22) Filed: Jun. 1, 2001

(65) Prior Publication Data

US 2002/0192248 A1 Dec. 19, 2002

(51) Int. Cl.[7] .............................. A61K 9/16; A61K 9/50
(52) U.S. Cl. ...................... 424/490; 424/401; 424/489; 424/59; 424/60; 424/78.03; 514/828; 514/844; 514/846
(58) Field of Search .................... 424/401, 489, 424/490, 59, 78.03, 60; 514/828, 844, 846

(56) References Cited

U.S. PATENT DOCUMENTS 117,435 A * 7/1871 Lillie ........................ 109/33

* cited by examiner

Primary Examiner—Jose' G. Dees
Assistant Examiner—Konata M. George
(74) Attorney, Agent, or Firm—Ezra Sutton (57) ABSTRACT

Optically-activated particles for use in cosmetic preparations. The optically-activated particles include a plurality of substrate particles selected from the group consisting of nylons, acrylics, polyesters, other plastic polymers, natural materials, regenerated cellulose, metals and minerals; an optical brightener chemically bonded to each of the plurality of substrate particles to form integral units in the form of optically-activated particles for diffusing light to reduce the visual perception of skin imperfections, including cellulite, shadows, skin discolorations, and wrinkles; and each of the optically-activated particles are encapsulated with a UV transparent coating to increase the diffusion light to further reduce the visual perception of the skin imperfections. The encapsulated optically-activated particles are able to absorb ultraviolet radiation and emit visible light; and the encapsulated optically-activated particles are able to both scatter and absorb light in a diffuse manner in order to reduce the visual perception of skin imperfections, including cellulite, wrinkles, shadows, and skin discolorations, when the optically-activated particles are applied to the skin surface. The encapsulated optically-activated particles are used in the making of cosmetic preparations such as skin lotions, creams, shampoos, body and skin rinses, bath gels, soaps, hair conditioners, color conditioners and rinses, hair color solutions, foundation powders (compressed or loose), tooth pastes, oral rinses, and any acceptable cosmetic vehicle or medium.

33 Claims, 5 Drawing Sheets

METHOD OF USING OPTICALLY-ACTIVATED PARTICLES IN COSMETIC PREPARATIONS

FIELD OF INVENTION

The present invention relates to optically-activated particles for use in cosmetic preparations to reduce the visual perception of skin imperfections. More particularly, these optically-activated and bonded particles increase the diffusion of light to reduce the visual perception of imperfections including, but not limited to, cellulite, wrinkles, discoloration by veins and arteries, shadows, blotchiness, pores, and follicles. Additionally, these optically-activated and bonded particles reduce the perception of wrinkles around the eyes and mouth, or mild discolorations such as mild scars and blotchiness of the skin in the face area, and can be used in an encapsulated or non-encapsulated form in the formation of various cosmetic preparations selected from the group consisting of skin lotions, creams, shampoos, body and skin rinses, bath gels, soaps, hair conditioners, color conditioners and rinses, hair color solutions, foundation liquids and powders (compressed or loose), tooth pastes and oral rinses.

BACKGROUND OF THE INVENTION

Natural-looking skin is influenced by a number of physiological and genetic factors. Standard definitions of beautiful skin include skin having a transparent quality with uniform undertones of color (i.e. rosy red cheeks). The basis for this natural-looking appearance is in the skin structure itself. The outer layer of human skin is a semi-transparent layer known as the stratum corneum. The transparency of the stratum corneum permits glimpses of the deeper layers of skin, where blood vessels and pigments reside; the reddish hue of the blood vessels' hemoglobin, and the brown/black hue of melanin, the primary skin pigment, combine to produce (what we view as) the skin's color. Of course, in addition to ideal skin having the transparent look with a uniform color distribution, it should also be smooth and even, with no apparent surface flaws. Only a few individuals can ever hope to meet such a standard without some outside assistance. Thus, a wide variety of cosmetics exist to help out where nature has failed.

Although makeup is worn on facial skin, it has not mimicked the actual appearance of natural skin beauty. Currently, the trend for cosmetic preparations have been to more natural-looking make-ups. In particular, one of the long-sought goals has been the development of a foundation that does not give the user a "made-up" look. In reality, however, it is difficult to accomplish the goal of achieving coverage of flaws and unevenness of skin tone, while still maintaining the vibrant look of clean bare skin. This is primarily because those components of makeups which provide the desired color and coverage, such as the titanium or iron oxide pigments, are largely opaque, and therefore obscure that sought-after vibrant transparency. Although in recent years, transparent pigments have become available, the coverage needed to mask flaws in the surface of the skin is frequently lacking.

There remains a need for cosmetic preparations that convey the perception that the user's skin has less wrinkles and less cellulite and less imperfections, obscuring discolorations to the skin and/or reducing skin blotchiness through the use of optically-activated and bonded particles. These optically-activated particles will allow for the emission and reflection of light and increase the diffusion of light to accomplish the foregoing.

DESCRIPTION OF THE PRIOR ART

The use of optical brightener compounds have been disclosed in the prior art. For example, U.S. Pat. No. 4,028,263 to GRAY discloses a bleaching and brightening detergent composition. This water soluble laundry detergent includes an organic anionic detergent, nonionic detergent or mixture thereof, a builder salt, preferably including a silicate, a peroxymonosulfate bleaching agent, a bromide promoter for the bleaching agent and one or more optical brighteners which are stable in the presence of the bleach and the promoter. This prior art patent does not teach or disclose the structure, configuration or composition of the optically-activated and bonded particles for use in cosmetic preparations as disclosed in the present invention.

U.S. Pat. No. 4,752,496 to FELLOWS et al discloses a method of applying cosmetics to a substrate and article. The cosmetics, which are normally dry, are combined with a liquid carrier and film forming agent and deposited onto a substrate. The film forming agent acts to micro encapsulate the cosmetic and lightly bond the cosmetic to the substrate. When the film forming agent dries, it protects the cosmetic. Thus, the cosmetic can be applied to a substrate and covered with a paperboard sheet. This prior art patent does not teach or disclose the structure, configuration or composition of the optically-activated and bonded particles for use in cosmetic preparations as disclosed in the present invention.

U.S. Pat. No. 6,117,435 to PAINTER et al discloses natural look cosmetic compositions. This topical application composition for use on skin includes silica beads having an inner core of silica, a middle layer of metal oxide, and an outer layer of silica; at least one interference pigment; and optionally, at least one non-interference pigment, in a cosmetically or pharmaceutically-acceptable formula. These cosmetic compositions confer a natural appearance to the user's skin, while also reducing the appearance of flaws or defects in the skin without conferring an opaque or made-up appearance. This prior art patent does not teach or disclose the structure, configuration or composition of the optically-activated and bonded particles for use in cosmetic preparations as disclosed in the present invention.

None of the aforementioned prior art patents teach or disclose the use of optically-activated and bonded particles for use in cosmetic preparations. Further, no prior art patents teach or disclose optically-activated particles which are able to both scatter and emit light in a diffuse manner in order to reduce the visual perception of shadows, skin discolorations, wrinkles and cellulite when applied to the skin surface.

Accordingly, it is an object of the present invention to provide optically-activated and bonded particles for use in cosmetic preparations, wherein the optically-activated particles are able to absorb ultraviolet radiation and emit visible light (releases energy in the form of light), and the optically-activated particles are also able to both scatter and emit light in a diffuse manner in order to reduce the visual appearance and perception of skin imperfections, such as shadows, skin discolorations, wrinkles and cellulite when applied to the skin surface.

Another object of the present invention is to provide optically-activated particles in which the substrate (particle) is pre-treated with a swelling agent in order to make the substrate particle wettable, electrostatically and ionically available for bonding, such that the swelling agent treatment of the particles swells the particles and they wet-out to prepare the particles for surface bonding by an optical brightener compound.

Another object of the present invention is to provide optically-activated particles that consist of a pre-treated substrate having an optical brightener compound (surface treatment) being applied and bonded to the substrate, such that the optical brightener compound is one or more molecules thick on the pre-treated substrate.

Another object of the present invention is to provide bonded optically-brightened particles that include an optical brightener compound selected from the group consisting of, but not limited to, Tinopal 5BM, Calcofluor White RC (Stilbene 4), Calcofluor CG (Stilbene 3) and Leucophor BSB Liquid, or equivalents.

Another object of the present invention is to provide optically-activated and bonded particles, having an optical brightener compound being permanently adhered and bonded to the substrate by the function of fixation by Van Der Waal's forces or ionic bonding or covalent bonding which makes the optical brightener compound at least one molecule thick bonded to the pre-treated substrate.

Another object of the present invention is to use optically-activated particles of a size that is below $30\mu$ (microns) (which is below the size that the eye can perceive) in cosmetic applications, wherein the preferred size of the bonded particle is in the range of $5\mu$ to $8\mu$ (microns) in diameter, and preferably the bonded particle is colorless, translucent, and non-visible to the human eye.

Another object of the present invention is to provide optically-activated and bonded particles having a substrate (particle) made of materials selected from the group consisting of nylons, acrylics, polyesters or other plastic polymers, natural materials, regenerated cellulose, metals, minerals or other suitable materials, and have an index of refraction greater than 1 in order that the image of the skin imperfection is bent away from the viewer's visual axis.

Another object of the present invention is to provide optically-activated and bonded particles, wherein the substrate (particle) configuration or structure may be in the form of a spheroid, a cuboid, a cylindrical-shaped particle, a tetrahedroid (pyramidally-shaped), a rhomboid, a plate, or other polygonal shaped configurations; and additionally, these particles may be solid or hollow in structure.

Another object of the present invention is to provide optically-activated particles that may be encapsulated with a UV transparent coating, such as, but not limited to, polyoxymethylene urea (PMU), wherein each capsule acts as a diffusion lens which increases the diffusion of emitted and reflected light to reduce the visual perception of skin imperfections, including cellulite, wrinkles, skin discolorations, and shadows when applied to the skin surface.

Another object of the present invention is to provide optically-activated particles that can be used in an encapsulated or non-encapsulated form in the formation of various cosmetic preparations selected from the group consisting of skin lotions, creams, shampoos, body and skin rinses, bath gels, soaps, hair conditioners, color conditioners and rinses, hair color solutions, foundation liquids and powders (compressed or loose), tooth pastes and oral rinses.

Another object of the present invention is to provide optically-activated particles that when used in cosmetic preparations reduce the visual perception of wrinkles (for example, around the eyes, areas of the arms, around the mouth, under the jaw), cellulite, or mild skin discolorations due to mild scars or varicose veins, and blotchiness of the skin as in the face area.

SUMMARY OF THE INVENTION

In accordance with the present invention, there is provided optically-activated particles for use in cosmetic preparations to reduce the visual perception of skin imperfections. The optically-activated particles include a plurality of substrate particles selected from the group consisting of nylons, acrylics, polyesters, other plastic polymers, natural materials, regenerated cellulose, metals and minerals; an optical brightener chemically bonded to each of the plurality of substrate particles to form integral units in the form of optically-activated particles for diffusing and emitting light to reduce the visual perception of cellulite, shadows, skin discolorations and wrinkles; and each of the optically-activated particles may be additionally, but need not be, encapsulated with a UV transparent coating to increase the diffusion of light to further reduce the visual perception of cellulite, shadows, skin discolorations and wrinkles. The encapsulated optically-activated particles are able to absorb ultraviolet radiation and emit visible light; and the encapsulated optically-activated particles are able to both scatter and emit light in a diffuse manner in order to reduce the visual perception of skin imperfections, including shadows, cellulite, wrinkles, and skin discolorations, when the optically-activated particles are applied to the skin surface. The encapsulated optically-activated particles are used in the making of cosmetic preparations such as skin lotions, creams, shampoos, body and skin rinses, bath gels, soaps, hair conditioners, color conditioners and rinses, hair color solutions, foundation liquids and powders (compressed or loose), tooth pastes and oral rinses.

BRIEF DESCRIPTION OF THE DRAWINGS

Further objects, features, and advantages of the present invention will become apparent upon the consideration of the following detailed description of the presently-preferred embodiment when taken in conjunction with the accompanying drawings, wherein.

DETAILED DESCRIPTION OF THE PREFERRED EMBODIMENT

The optically-activated particles 10 for use in cosmetic preparations 12 of the preferred embodiment of the present invention are represented in detail by FIGS. 1 through 4 of the drawings. These optically-activated and bonded particles 10 allow for the emission and reflection of light together with the diffusion of light 40 for the purpose of reducing the visual perception of cellulite, wrinkles, shadows, skin discolorations by veins and arteries, and the obscuring of particular visual attributes of the skin support surface 14. Further, these optically-activated and bonded particles reduce the perception of wrinkles 16 around the eyes and mouth, areas of cellulite, mild discolorations on the skin such as mild scars or abrasions and blotchiness of the skin such as occurs in, but not limited to, the face area.

Figure 1:
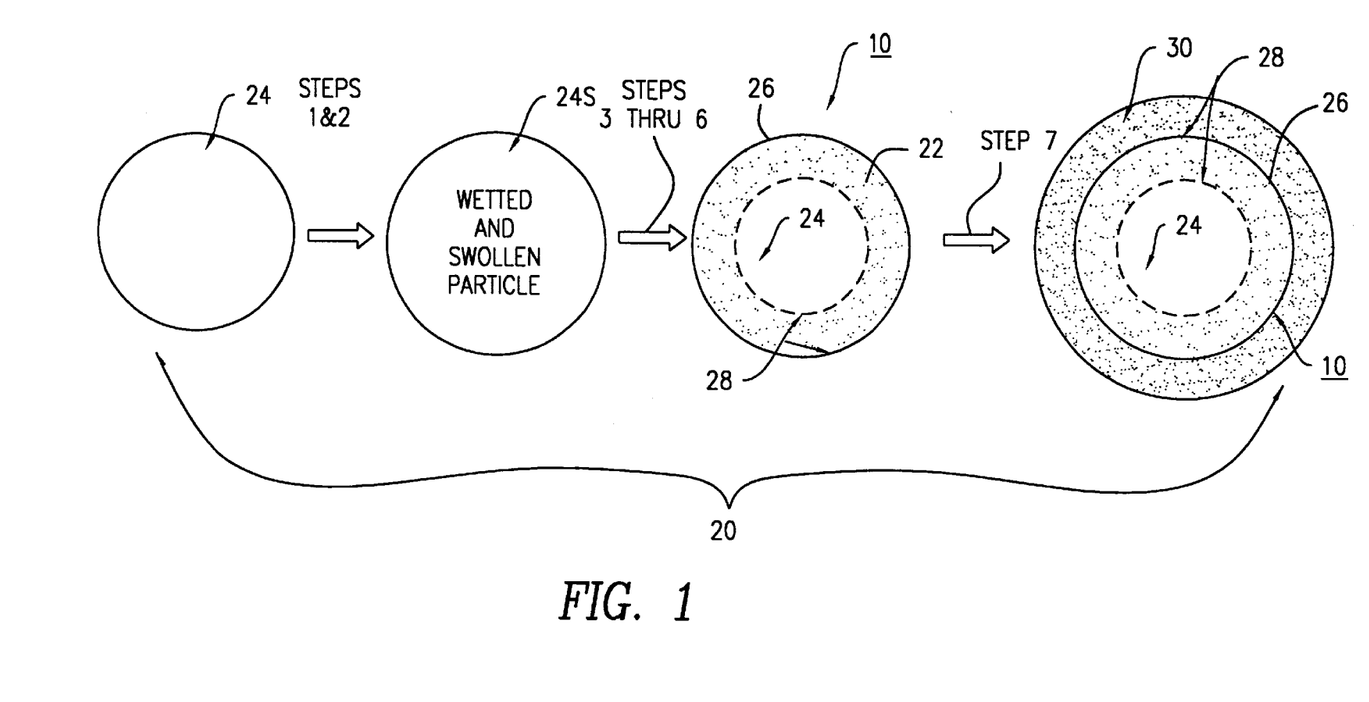
FIG. 1 is a schematic representation of the chemical process of converting a nylon spheroid particle to an encapsulated optically-activated particle with several intervening processing steps.
Figure 2:
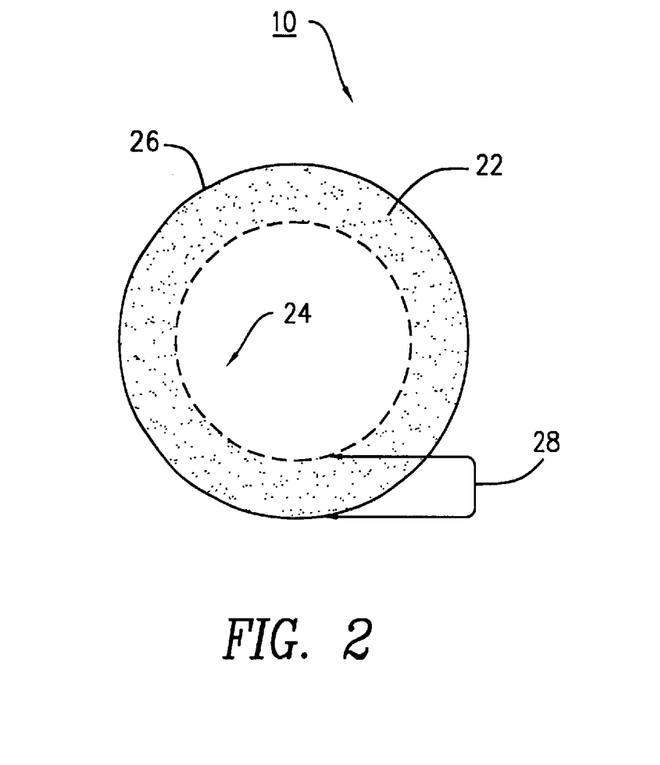
FIG. 2 is an enlarged sectional view of the optically-activated particle of the preferred embodiment of the present invention showing the optical brightener material reacted and bonded within the outermost layers of the nylon spheroid particle.
Figure 3:
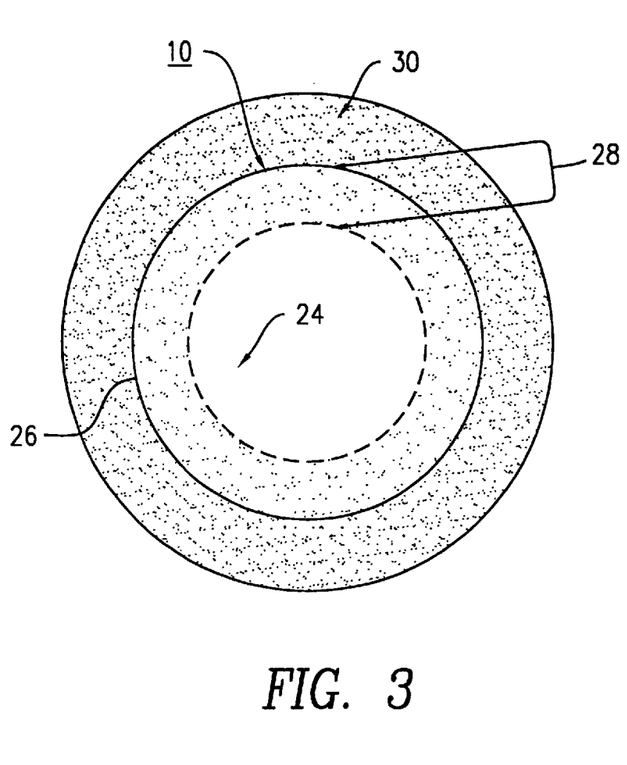
FIG. 3 is an enlarged sectional view of the optically-activated particle of the preferred embodiment of the present invention showing the optically-activated particle encapsulated.
Figure 4:
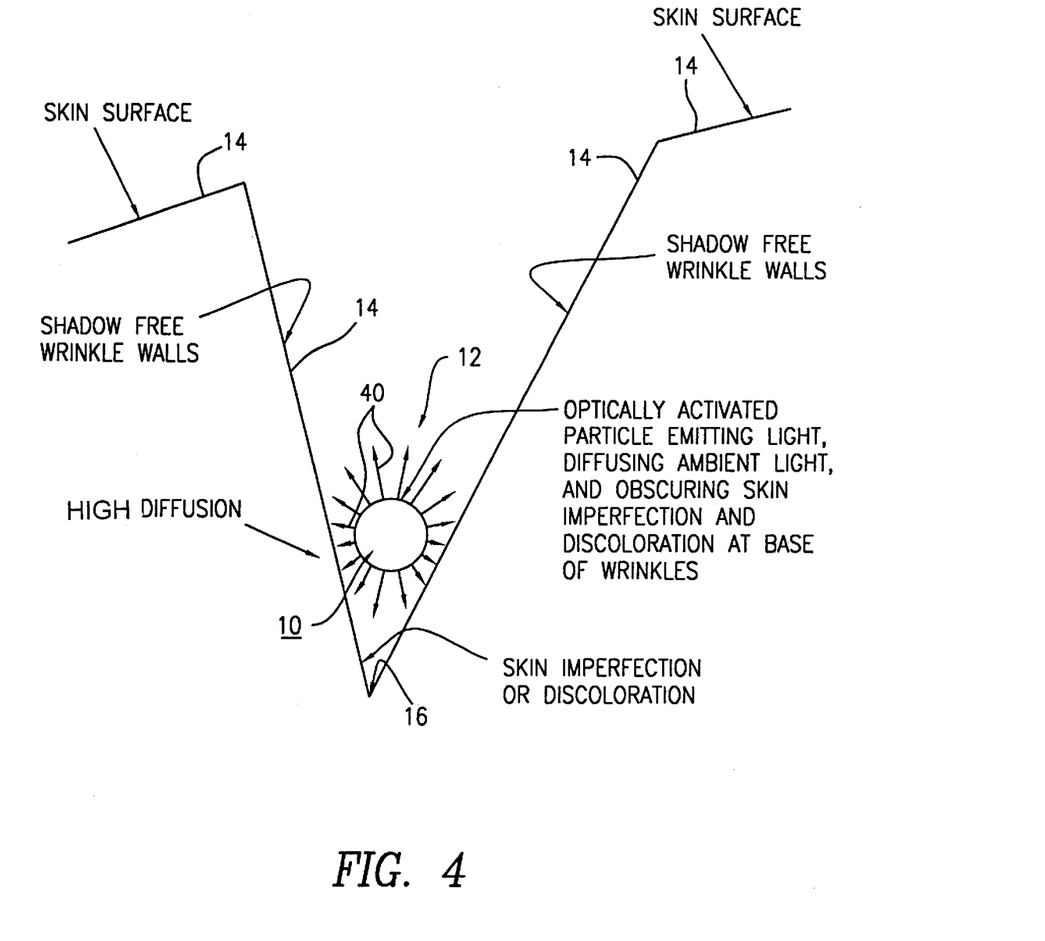
FIG. 4 is an enlarged sectional view of the optically-activated particle of the present invention showing the optically-activated particle within a crease of a user's outer skin layer in which the optically-activated particle is reflecting and emitting light to decrease the shadow effect and any skin imperfection.
Figure 5:
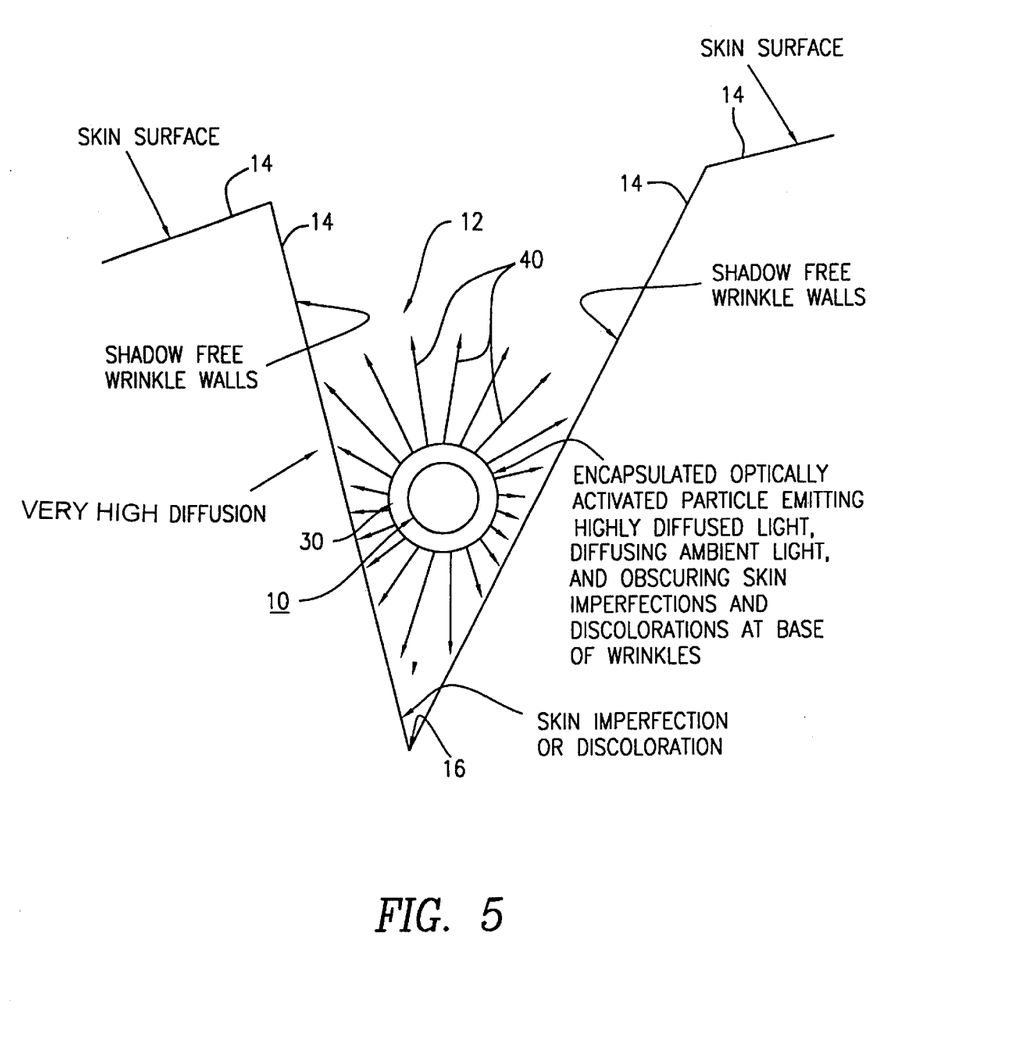
FIG. 5 is an enlarged sectional view of the optically-activated particle of the present invention showing the encapsulated optically-activated particle within a crease of a user's outer skin layer in which the encapsulated optically-activated particle is reflecting and emitting light to further decrease the shadow effect of the skin imperfection.
Figure 6:
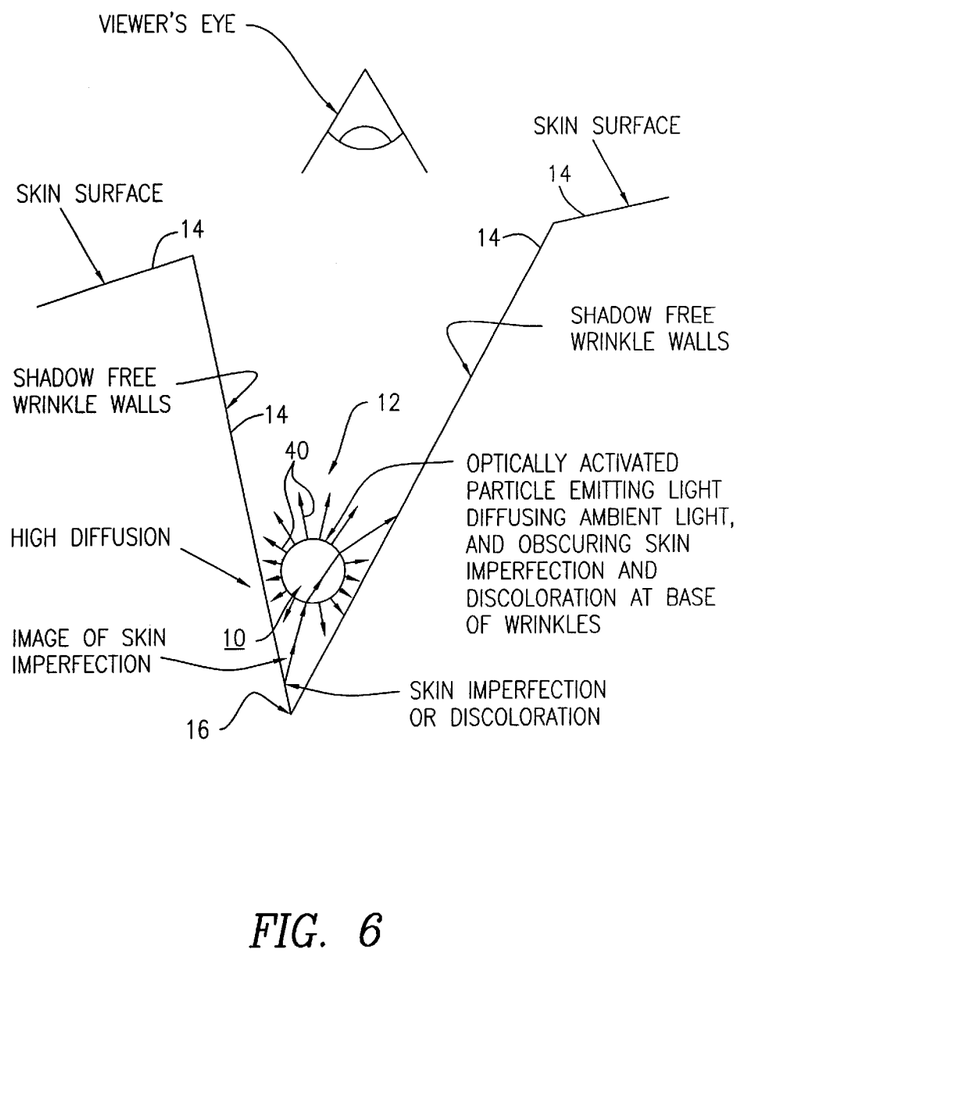
FIG. 6 is an enlarged view showing how the image of the skin imperfection is bent by the optically-activated particle and is not in the viewer's visual axis.

This optically-activated particle 10 is created in a chemical process 20, as shown in FIGS. 1 to 3 of the drawings, under heat, temperature, and time (t) using an optical brightener compound 22 on a pre-treated substrate particle 24. The substrate particle 24 cannot have a refractive index of 1.0, any other refractive index greater than 1.0 is suitable for use. The optical brightener compound 22 is chemically bonded to the substrate 24 (i.e. a nylon spheroid particle) by covalent or ionic bonding, such that the optical brightener 22 is inseparable from the nylon particle 24 and becomes part of the finished optically-activated particle 10. When using a spheroid as the substrate particle 24, the finished optically-activated particle 10 diffuses light 40 in a radially extending pattern, as shown in FIGS. 4 and 5 of the drawings. The outermost perimeter surface/section 26 of the optically-activated particle 10 has a permanent perimeter section 28 of the optically-activated nylon particle 24. The optical brightener compound 22 is bonded to and becomes an integral part of the nylon polymer matrix 24 and a bonded particle 10 is created. The optical brightener compound 22 is not separable or removable from the optically-activated bonded particles 10 that are created. The optical brightener material 22 is reacted with the outermost layers (perimeter section) 28 of the nylon particle 24 and is one or more molecules thick, as depicted in FIG. 1 of the drawings. The optically-activated and bonded particle 10 may be encapsulated with a UV transparent coating 30, such as a polyoxymethylene urea (PMU), wherein the capsule acts as a diffusion lens which increases the effective diffusion pattern of light 40. Thus, the optically-activated particles 10 reduce the visual perception of cellulite, wrinkles, discoloration and shadows when applied to the skin surface 14, as depicted in FIGS. 4 to 6 of the drawings.

The chemical process 20 for making the optically-activated particles 10, as shown in FIG. 1 of the drawings, includes the following processing steps:

1. Mixing swelling agents and nylon-12 (substrate) particles, such as, but not limited to, ORGASOL® 2002 UD NAT COS, having an approximate 5 micron diameter to form a nylon substrate paste or slurry.
2. A batch of water is heated to 180° F. in which the nylon slurry is dispersed and mixed into the heated water to wet-out and swell the nylon-12 substrate particles 24, as shown in FIG. 1. The mixture of heated water and the nylon slurry is continuously mixed using a propeller to form a complex solution.
3. A charge of an optical brightener, such as, but not limited to, LEUCOPHOR BSB®, is added to the mixture of heated water and the nylon slurry to form a complex solution. This mixture containing heated water, the nylon slurry and the optical brightener is also continually mixed using a propeller. This mixture is held at 180° F. for at least 30 minutes.
4. This mixture containing the heated water, the nylon slurry and the optical brightener is decanted using a vacuum assisted filter device. The decanted particulate material 10 remaining on the filter is flushed with fresh water until the particulate material 10 becomes clear.
5. The particulate material (optically-activated particles) 10 is then dried using a forced air oven.
6. The dried particulate material in the form of optically-activated particles 10 are then dispersed, added or mixed into lotions, creams, shampoos, conditioners and the like for formulating various cosmetic preparations.
7. Optionally, the dried particulate material in the form of optically-activated particles 10 are then encapsulated using a UV transparent coating 30, such as, but not limited to, polyoxymethylene urea (PMU). This encapsulation of the optically-activated particles 10 is used to increase light diffusion in order to create an increased "softness effect" of the reflected and emitted light coming from the capsulated particulate material 10 by increasing light diffusion. The capsule size is below 10 microns in diameter.

The chemical composition of the solution containing the heated water, the nylon substrate slurry and the optical brightener is as follows:

| | |
|---|---|
| a) Water | 50.0% to 69.9% |
| b) Nylon 12 substrate slurry containing | 30.0% |
| b1) Swelling agents: | 10.0% |
| b2) Nylon 12 particles: | 20.0% |
| c) Optical brightener agent | 0.1% to 20.0% |
| | 100.0% |

The chemical composition of the dry reacted optically-activated particles is as follows:

| | |
|---|---|
| a) Optical brightener agent | 0.1% to 20.0% (on a dry basis) |
| b) Nylon 12 substrate | 80.0% to 99.9% |

OPERATION OF THE PRESENT INVENTION

The optically-activated particles 10 are used in cosmetic preparations 12 to reduce the visual perception of skin imperfections, such as cellulite, shadows, wrinkles and mild skin discolorations such as mild scars, varicose veins, and blotchiness of the skin, such as, but not limited to, the face area. The uniqueness of using these optically-activated particles 10 within a cosmetic preparation 12 is the emission, reflection and diffusion of light 40 for reducing the perception of skin imperfections and for obscuring of the skin below the particle. The substrate particles 24 have an index of refraction greater than 1.0 in order that the image of the skin imperfection is bent away from the viewer's visual axis, as shown in FIG. 6. As shown, the image of the skin imperfection is bent by the particle into the wall of the wrinkle so it is not seen by the eye of the viewer. The particle itself is preferably colorless, translucent, and non-visible to the human eye (under 30µ). Thus, the human eye only sees the emitted light 40.

When the optically-activated particles 10 are exposed to ambient UV, they absorb the UV as energy, and release light 40 in a diffused manner, creating a radiant release of light 40, as shown in FIGS. 3 and 4 of the drawings. Thus, the bonding of the optical brightener to the substrate particle 24 creates a radiant emissive source of light 40 having high diffusion. This light 40 is minuscule, and may not be consciously perceived by the viewer, and is interpreted by the visual center of perception and images (the visual cortex). Thus, particle 10 is an optical function for the cosmetic product 12 which obscures skin imperfections and reduces the visual perception of skin imperfections. The primary format of the present invention is to use the particles 10 in a cosmetic vehicle.

These particles 10 may be encapsulated in a UV transparent capsule 30, such as but not limited to polyoxymethylene urea (PMU). The capsule acts as a diffusion lens increasing the effective diffusion pattern of light 40, which further reduces the visual perception of cellulite, wrinkles, shadows and skin discoloration regardless of the configuration of the skin surface 14. An additional purpose of joining of the optical brightener 22 to a substrate 24 (such as nylon spheroids) by ionic bonding is to create particles 10 which are non-reactive and inert for use in cosmetic preparations.

ADVANTAGES OF THE PRESENT INVENTION

Accordingly, an advantage of the present invention is that it provides for optically-activated and bonded particles for use in cosmetic preparations, wherein the optically-activated particles are able to absorb ultraviolet radiation and emit visible light (releases energy in the form of light), and the optically-activated particles are also able to scatter both incident and emitted light in a diffuse manner in order to reduce the appearance and visual perception of skin imperfections, including shadows, skin discolorations, wrinkles, and cellulite, when applied to the skin surface, as well as obscure the skin beneath the particles.

Another advantage of the present invention is that it provides for optically-activated particles in which the substrate (particle) is pre-treated with swelling agents in order to make the substrate particle water wettable, electrostatic and ionically available for bonding, such that the treatment of the particles swells the particles and they wet-out to prepare the particles for surface bonding by an optical brightener compound.

Another advantage of the present invention is that it provides for optically-activated particles that consist of a pre-treated substrate having an optical brightener compound surface treatment) being applied and bonded to the substrate, such that the optical brightener compound is one or more molecules thick on the pre-treated substrate.

Another advantage of the present invention is that it provides bonded optically-brightened particles that include an optical brightener compound selected from, but not limited to, the group consisting of Tinopal 5BM, Calcofluor White RC (Stilbene 4), Calcofluor CG (Stilbene 3) and Leucophor BSB Liquid, or equivalents.

Another advantage of the present invention is that it provides a substrate of optically-activated and bonded particles, with an optical brightener compound being permanently adhered and bonded to the substrate by the function of fixation by Van Der Waal's forces or ionic bonding or covalent bonding which makes the optical brightener compound at least one molecule thick adherence to the pre-treated substrate.

Another advantage of the present invention is that it uses optically-activated particles of a size that is below 30μ (microns) which is below the size that the eye can perceive, wherein the preferred size of the bonded particle is in the range of 5μ to 8μ (microns) in diameter, and preferably the bonded particle is colorless, translucent, and non-visible to the human eye.

Another advantage of the present invention is that it provides optically-activated and bonded particles, having a substrate (particle) made of materials selected from the group consisting of nylons, acrylics, polyesters or other plastic polymers, natural materials, regenerated cellulose, metals, minerals or other suitable materials, and have an index of refraction greater than 1 in order that the image of the skin imperfection is bent away from the viewer's visual axis.

Another advantage of the present invention is that it provides optically-activated and bonded particles, wherein the substrate (particle) configuration or structure may be in the form of, but not limited to, a spheroid, a cuboid, a cylindrical-shaped particle, a tetrahedroid (pyramidally-shaped), a rhomboid, a plate, or other polygonal shaped configurations; and additionally, these particles may be solid or hollow in structure.

Another advantage of the present invention is that it provides optically-activated particles that may be encapsulated with a UV transparent coating, such as, but not limited to, polyoxymethylene urea (PMU), wherein each capsule acts as a diffusion lens which increases the diffusion of light to reduce the visual perception of skin imperfections, such as cellulite, wrinkles, skin discolorations and shadows when applied to the skin surface.

Another advantage of the present invention is that it provides optically-activated particles that can be used in an encapsulated or non-encapsulated form in the formation of various cosmetic preparations selected from the group consisting of skin lotions, creams, shampoos, body and skin rinses, bath gels, soaps, hair conditioners, color conditioners and rinses, hair color solutions, foundation powders (compressed or loose), tooth pastes and oral rinses.

Another advantage of the present invention is that it provides optically-activated particles that when used in cosmetic preparations reduce the visual perception of skin imperfections, such as wrinkles (for example, around the eyes, areas of the arms, around the mouth, under the jaw), cellulite, or mild skin discolorations due to mild scars or varicose veins, and blotchiness of the skin as in the face area.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. Optically-activated particles for use in cosmetic preparations to reduce the visual perception of skin imperfections, comprising:

a) a plurality of substrate particles selected from the group consisting of nylons, acrylics, polyesters, other plastic polymers, natural materials, regenerated cellulose, metals and minerals; wherein said substrate particles have an index of refraction greater than 1.0;

b) an optical brightener chemically bonded to each of said plurality of substrate particles to form integral units in the form of optically-activated particles for diffusing and emitting light to reduce the visual perception of skin imperfections by bending the image of the skin imperfections away from the viewer's visual axis; and c) each of said optically-activated particles being encapsulated with a UV transparent coating to increase the diffusion of light to further reduce the visual perception of the skin imperfections.

2. Optically-activated particles in accordance with claim 1, wherein each of said plurality of substrate particles is at least 5μ (microns) in size, but below 30μ in size.

3. Optically-activated particles in accordance with claim 1, wherein each of said plurality of substrate particles has a configuration or structure selected from the group consisting of a spheroid, a cuboid, a cylindrical-shaped particle, a tetrahedroid, a rhomboid, a plate, and other polygonal shaped configurations and equivalents.

4. Optically-activated particles in accordance with claim 1, wherein each of said plurality of substrate particles is solid or hollow in structure.

5. Optically-activated particles in accordance with claim 1, wherein said plurality of substrate particles are pre-treated with one or more swelling agents to make said plurality of substrate particles water wettable, swollen, electrostatic and ionically available, wherein said plurality of pre-treated substrate particles are ready for surface bonding by said optical brightener.

6. Optically-activated particles in accordance with claim 1, wherein said optical brightener is permanently bonded to said plurality of substrate particles to make said optical brightener at least one molecule thick on said plurality of substrate particles.

7. Optically-activated particles in accordance with claim 1, wherein said optical brightener is selected from the group consisting of Tinopal 5BM, Calcofluor White RC (Stilbene 4), Calcofluor CG (Stilbene 3) and Leucophor BSB liquid.

8. Optically-activated particles in accordance with claim 1, wherein each of said optically-activated particles is colorless, translucent, and non-visible to the human eye.

9. Optically-activated particles in accordance with claim 1, wherein each of said optically-activated particles has a preferred range of 5μ to 8μ (microns) in size.

10. Optically-activated particles in accordance with claim 1, wherein each of said optically-activated particles has a configuration or structure selected from the group consisting of a spheroid, a cuboid, a cylindrical-shaped particle, a tetrahedroid, a rhomboid, a plate, and other polygonal shaped configurations.

11. Optically-activated particles in accordance with claim 1, wherein each of said optically-activated particles is solid or hollow in structure.

12. Optically-activated particles in accordance with claim 1, wherein each of said optically-activated particles is a nylon-based spheroid for radially diffusing the tight from each of said optically-activated particles to reduce the visual perception of skin imperfections.

13. Optically-activated particles in accordance with claim 1, wherein said optically-activated particles are used in the making of cosmetic preparations selected from the group consisting of skin lotions, creams, shampoos, body and skin rinse, bath gels, soaps, hair conditioners, color conditioners and rinses, hair color solutions, foundation liquids and powders (compressed or loose), tooth pastes and oral rinses.

14. Optically-activated particles in accordance with claim 1, wherein said optically-activated particles both scatter and emit light in a diffuse manner to reduce the visual perception of skin imperfections, including cellulite, wrinkles, skin discolorations, and shadows, when said optically-activated particles are applied to the skin surface.

15. Optically-activated particles in accordance with claim 1, wherein said optically-activated particles absorb ultraviolet radiation and emit and diffuse visible light.

16. Optically-activated particles in accordance with claim 1, wherein said UV transparent coating is a polyoxymethylene urea (PMU).

17. Optically-activated particles in accordance with claim 1, wherein each of said encapsulated optically-activated particles is a nylon-based spheroid for radially enhancing the diffusing of light from each of said encapsulated optically-activated particles to reduce the visual perception of skin imperfections.

18. Optically-activated particles in accordance with claim 1, wherein each of said encapsulated optically-activated particles have a size in the range of 5μ to 8μ (microns).

19. Optically-activated particles in accordance with claim 1, wherein said encapsulated optically-activated particles are used in the making of cosmetic preparations selected from the group consisting of skin lotions, creams, shampoos, body and skin rinses, bath gels, soaps, hair conditioners, color conditioners and rinses, hair color solutions, foundation liquids and powders (compressed or loose), tooth pastes, oral rinses, and any cosmetically-acceptable vehicles.

20. Optically-activated particles in accordance with claim 1, wherein said encapsulated optically-activated particles absorb ultraviolet radiation and emit visible light in a diffuse manner, and wherein said encapsulated optically-activated particles both scatter and emit light in a diffuse manner to reduce the visual perception of skin imperfections when said encapsulated optically-activated particles are applied to the skin surface.

21. A method of making optically-activated particles for use in cosmetic preparations for reducing the visual perception of skin imperfections, comprising the steps of:
  a) coating a plurality of substrate particles with one or more anhydrous solvents to form a slurry;
  b) adding said slurry to water to form a complex solution and heating said complex solution to wet-out and swell said plurality of substrate particles to form a plurality of wetted and swollen substrate particles;
  c) reacting said plurality of wetted and swollen substrate particles with an optical brightener being added to said complex solution and said optical brightener being in the range of 0.10% to 20.0% by weight of said complex solution;
  d) heating said complex solution for at least 30 minutes for reacting said optical brightener with said plurality of wetted and swollen substrate particles to form a plurality of optically-activated particles in said complex solution; and
  e) separating said complex solution from said plurality of optically-activated particles having said optical brightener being in the range of 0.10% to 20.0% by dry weight composition and said substrate particles being in the range of 80.0% to 99.9% by dry weight composition for use in making cosmetic preparations.

22. A method of making optically-activated particles in accordance with claim 21, wherein said step of coating said plurality of substrate particles with said one or more anhydrous solvents includes one or more glycol derivatives to form said slurry.

23. A method of making optically-activated particles in accordance with claim 21, wherein said step of adding said slurry to said water further includes the step of mixing said complex solution by a mechanical propeller for enhancing the wetting-out and swelling of said plurality of substrate particles.

24. A method of making optically-activated particles in accordance with claim 21, wherein said steps of reacting said plurality of wetted and swollen substrate particles with said optical brightener being added to said complex solution further includes the step of blending said plurality of wetted and swollen substrate particles and said optical brightener within said complex solution by a mechanical propeller for enhancing the reacting of said optical brightener with said plurality of wetted and swollen substrate particles in forming said plurality of optically-activated particles in said complex solution or equivalents.

25. A method of making optically-activated particles in accordance with claim 21, wherein said step of reacting said plurality of wetted and swollen substrate particles with said optical brightener includes said optical brightener being selected from the group consisting of Tinopal 5BM, Calcofluor White RC (Stilbene 4), Calcofluor CG (Stilbene 3) and Leucophor BSB liquid.

26. A method of making optically-activated particles in accordance with claim 21, wherein said step of separating said complex solution from said plurality of optically-activated particles includes the steps of filtering and drying said complex solution to separate said plurality of optically-activated particles from said complex solution.

27. A method of making optically-activated particles in accordance with claim 21, further including the step of making said plurality of dry optically-activated particles into cosmetic preparations selected from the group consisting of skin lotions, creams, shampoos, body and skin rinses, bath gels, soaps, hair conditioners, color conditioners and rinses, hair color solutions, foundation powders (compressed or loose), tooth pastes, oral rinses, or any acceptable-cosmetic vehicle or medium.

28. A method of making optically-activated particles in accordance with claim 21, wherein said step of separating said complex solution from said plurality of optically-activated particles forms a plurality of dry optically-activated particles; and further including the step of encapsulating said plurality of dry optically-activated particles using a UV transparent coating to form a plurality of encapsulated optically-activated particles.

29. A method of making optically-activated particles in accordance with claim 28, wherein said step of encapsulating said plurality of dry optically-activated particles is performed using a polyoxymethylene urea (PMU) coating as said UV transparent coating.

30. A method of optically-activated particles in accordance with claim 28, further including the step of processing said plurality of encapsulated optically-activated particles into cosmetic preparations selected from the group consisting of skin lotions, creams, shampoos, body and skin rinses, bath gels, soaps, hair conditioners, color conditioners and rinses, hair color solutions, foundation powders (compressed or loose), tooth pastes, oral rinses, or any acceptable-cosmetic vehicle or medium.

31. A method of using a composition having optically-activated substrate particles for use in cosmetic applications in order to reduce the visual perception of skin imperfections, wherein said composition comprises:

a) a plurality of substrate particles selected from the group consisting of nylons, acrylics, polyesters, other plastic polymers, natural materials, regenerated cellulose, metals and minerals, wherein said substrate particles have an index of refraction greater than 1.0 in order that the image of the skin imperfection is bent away from the viewer's visual axis;

b) an optical brightener chemically bonded to each of said plurality of substrate particles to form integral units in the form of optically-activated particles for diffusing light to reduce the visual perception of skin imperfections;

c) each of said optically-activated particles being encapsulated with a UV transparent coating to increase the diffusion of light to further reduce the visual perception of the skin imperfections; and said method comprising the step of applying said composition to a person s skin to reduce the visual perception of skin imperfections by bending the image of the skin imperfection away from the viewer's visual axis.

32. Optically-activated particles in accordance with claim 1, wherein said skin imperfections include shadows, skin discolorations, cellulite, wrinkles, open pores, hair follicles and blotchiness.

33. A method of making optically-activated particles in accordance with claim 31, wherein said skin imperfections include shadows, skin discolorations, cellulite, wrinkles, open pores, hair follicles and blotchiness.

* * * * *